United States Patent
Wang et al.

(10) Patent No.: US 7,718,427 B2
(45) Date of Patent: May 18, 2010

(54) **ESTABLISHED CELL LINES FROM *LYMANTRIA XYLINA***

(75) Inventors: Chung-Hsiung Wang, Taipei (TW); Chih-Yu Wu, Taipei (TW); Shih-Chia Yeh, Taipei (TW)

(73) Assignee: National Taiwan University, Taipei (TW)

( * ) Notice: Subject to any disclaimer, the term of this patent is extended or adjusted under 35 U.S.C. 154(b) by 355 days.

(21) Appl. No.: 11/839,500

(22) Filed: Aug. 15, 2007

(65) Prior Publication Data

US 2008/0299653 A1    Dec. 4, 2008

(30) Foreign Application Priority Data

May 28, 2007 (TW) ............................... 96118957 A (51) Int. Cl.
*C12N 5/07* (2010.01)
*C12N 5/00* (2006.01)

(52) U.S. Cl. ...................................... 435/348; 435/325

(58) Field of Classification Search ................. 435/348, 435/325
See application file for complete search history.

(56) References Cited

OTHER PUBLICATIONS

Wu and Wang (2006) J. Invert. Pathol., vol. 93, 186-191.*
Wu et al., Journal of Invertebrate Pathology, vol. 93, (2006), pp. 186-191.

* cited by examiner

*Primary Examiner*—Anne Marie S Wehbe
(74) *Attorney, Agent, or Firm*—Birch, Stewart, Kolasch & Birch, LLP (57) ABSTRACT

The present invention relates to *Lymantria xylina* cell lines established from pupal tissues of *L. xylina* Swinhoe, including NTU-LY-1, NTU-LY-2, NTU-LY-3, and NTU-LY-4. These four cell lines were confirmed to be newly established cell lines derived from *L. xylina* by random amplified polymorphic DNA-polymerase chain reaction (RAPD-PCR) and isozyme analysis. The genotypes and characteristics of the abovementioned cell lines are totally different from other insect cell lines. In addition, these four *L. xylina* cell lines are susceptible to insect baculovirus of *L. xylina* multiple nucleopolyhedrovirus (LyxyMNPV), LdMNPV-like virus, PenuMNPV, as well as microsporidia of *Nosema* sp. (isolated from *Eurema blanda*) and *N. bombycis* and the like. Therefore the invention can be applied in multiplication of the abovementioned insect-pathogenic microorganisms to produce biopesticides in pest control. In addition, the cell lines can also be used as hosts for the expression vectors of said baculovirus to produce recombinant proteins.

12 Claims, 7 Drawing Sheets

ESTABLISHED CELL LINES FROM *LYMANTRIA XYLINA*

BACKGROUND OF THE INVENTION

1. Field of the Invention

The present invention relates to cell lines established from insect tissues, especially relates to cell lines from *L. xylina* with high susceptibility to insect pathogenic microorganisms. These cell lines can be used in the mass production of insect pathogenic microorganisms and recombinant proteins.

2. The Prior Arts

The casuarina moth, *Lymantria xylina* Swinhoe (Order: Lepidoptera, Family: Lymantriidae, Genus: *Lymantria*), is one of the most damaging pests in the forest, mainly distributes in Taiwan, Japan, India, and the eastern coast of mainland China, which can eat all the leaves and twigs off a tree, stunt the growth and cause the death of plants. The toxic spines or hairs of *L. xylina* caterpillars provoke a cutaneous and immune reaction in human. Due to the extension of its host plant range and the increasing agricultural loss, this moth now becomes a significant quarantine pest.

The chemical insecticides are often used to kill the larvae of *L. xylina* to control the spread of *L. xylina*, which not only cause the problems of drug resistance and residual effects, but also involve in environmental contamination and resurgence of secondary insect pest species. Therefore, alternative control methods are studied to replace or to reduce the dependence of chemicals. Among them, using the insect pathogenic microorganisms to produce biopesticides is the most important method. Studies have revealed an lethal epizootic disease, nucleopolyhedrosis, of *L. xylina* larvae occurs from spring to early summer in Taiwan and mainland China, and the key pathogen was found to be *L. xylina* multiple nucleopolyhedrovirus (LyxyMNPV). LyxyMNPV is a rod-shaped virus and belongs to the baculovirus family. After infecting the host, the baculovirus buds budded virus (BV) to spread infection between cells inside the insect body and expresses the polyhedrin gene to produce polyhedrin. Multiple virions are found embedded in polyhedrin matrix in the nucleus known as occlusion bodies (OBs), which is also referred to as polyhedron inclusion bodies (PIBs), and the virus is therefore named as the nucleopolyhedrovirus (NPV).

The occlusion bodies can be released to outside from the lysed infected insects and further infect other insects to induce an epizootic disease. The spread of the disease is not only caused by horizontal transmission of NPV either from insect to insect or ingestion of the viral particles, but also be spread through vertical transmission from generations to generations. NPV are highly host-specific, have very species-specific tropisms among the invertebrates which cause no harm to humans, animals or other organisms. Studies have shown that the LyxyMNPV effectively suppress *L. xylina* population in field trials. Therefore the LyxyNPV can be used as a safe biological control agent in controlling the *L. xylina* populations. In addition, LyxyMNPV belongs to the baculovirus family, the latter is a core expression system of foreign protein production for medical and industrial applications, indicates the potential of being a recombinant protein expression system for LyxyMNPV.

Other than NPV, one of another main causes for epizootic disease is microsporidiosis inducing by microsporidia. The *Nosema* genus is the most common pathogen for microsporidiosis involved in the epizootic. Microsporidia propagate and infect host cells through the passages of meronts and spores. Since microsporidia play an important role in the regulation of insect populations, they have the potential to be used as biopesticides and be applied in pest control.

The insect pathogenic microorganisms can either be used as biopesticides in agriculture and forest pests, or be applied as a subject in studies of pathogenic genes and viral expression vectors for industrial or medical purposes. The priority is to have enough sources of the insect pathogenic microorganisms. The insect-infected baculovirus needs to be cultured in live cells, such as propagation through insect larvae or cell line culture. For example, multiplication of LyxyMNPV involved the large-scale rearing of *L. xylina* larvae. This process is labor intensive and several challenges need to be met (e.g. the conditions for breaking embryonic diapause the development of artificial diets, and the prevention of epizootic diseases) to obtain a reliable source of the host insect. In vitro production of LyxyMNPV in a highly susceptible insect cell line is an alternative solution. This strategy possesses advantages of: no contamination from other microorganisms during cultivation, screening and maintaining highly virulent LyxyMNPV strains.

Insect cell lines have the advantage for in vitro culture of pathogenic microorganisms. Hundreds of continuous cell lines have been established from over 100 insect species since Grace et al. established the first insect cell line in 1962 (Lynn, D. E., Development of insect cell lines: virus susceptibility and applicability to prawn cell culture. Methods in Cell Sci., 21(4):173-81.1999). These cell lines have been used broadly in researches of physiology, histology, embryology, molecular biology, pathology and insect virology. The baculovirus expression vectors and the production of recombinant proteins also need insect cell lines. However, there is no LyxyMNPV permissive cell line established so far. Besides, virus has specificity to host cell, each cell has different susceptibility to different virus. Therefore, establishment of proper insect cell line is critical for basic research and the following application.

In summary, the production of biopesticides can be enhanced to reach the safety and pest control purposes if a highly susceptible cell line to LyxyMNPV or other insect pathogenic microorganisms is established. The cell line can also be applied in the expression system of insect baculovirus to produce recombinant proteins for medical or research purposes.

SUMMARY OF THE INVENTION

The objective of the present invention is to provide a LyxyMNPV or other insect pathogenic microorganisms highly susceptible cell line for multiplication of insect pathogenic microorganisms and production of recombinant proteins, or to stably produce insect baculovirus and microsporidia through in vitro culture, followed by application in the expression system of insect baculovirus to produce recombinant proteins for medical or research purposes.

To fulfill the abovementioned objectives, the invention provides cell lines from *L. xylina* for production of insect pathogenic microorganisms and recombinant proteins, which was isolated from the internal tissues of 2- to 4-day-old pupae of *L. xylina*. The primary culture of pupal tissues were subcultured after 1 month incubation, followed by several passages with media of different composition and ratio at defined intervals. Four continuous cell lines from different primary cultures have been successfully established and are designated NTU-LY-1, NTU-LY-2, NTU-LY-3, and NTU-LY-4, respectively. Among them, the NTU-LY-4 was deposited in Biosource collection and research center (BCRC) of Food Industry Research and Development Institute (FIRDI) under an accession number of BCRC 960290.

The morphologies of these cell lines were studied, which consist primarily of round cells, followed by spindle-shaped and giant cells. On the other hand, the RAPD-PCR analysis showed similar DNA profiles for the four newly established *L. xylina* cell lines and the *L. xylina* larva from which indicated that their genotypes were essentially identical and all cells of NTU-LY-1 to NTU-LY-4 are derived from the *L. xylina*. Nevertheless, no enzyme patterns of the four *L. xylina* cell lines were similar to that of IPLB-LD-652Y (*L. dispar* cell line, Goodwin et al., 1978) from the isozyme analysis, which verified that the NTU-LY-1 to NTU-LY-4 are new cell lines.

The characteristics of these cell lines were studied. NTU-LY-4 cells showed a faster growth rate than the other LY cells from the growth curves, indicated the industrial application for NTU-LY-4 cells. All of the newly established cell lines of NTU-LY-1 to NTU-LY-4 were susceptible to the LyxyMNPV from the viral susceptibility test. Furthermore, these cell lines can be infected with LdMNPV-like virus and PenuMNPV, and were also susceptible to *Nosema* sp. (isolated from *Eurema blanda*) and *N. bombycis*. This shows that the invention successfully established cell lines for propagation of LyxyMNPV and the abovementioned insect-pathogenic microorganisms through in vitro culture.

The *L. xylina* cell lines established in the invention can be used for in vitro culture of LyxyMNPV and many insect-pathogenic microorganisms such as insect baculovirus of LdMNPV-like virus and PenuMNPV, as well as microsporidia of *Nosema* sp. (isolated from *Euerna blanda*) and *N. bombycis* and the like. The mass production of these microorganisms can be developed to be biopesticides and applied in pest control. The cell line can also be used as hosts for the expression vectors of said baculovilus to produce recombinant proteins for medical or research purposes.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The related drawings in connection with the detailed description of the present invention to be made later are described briefly as follows, in which.

DETAILED DESCRIPTION OF THE PREFERRED EMBODIMENT

The invention established 4 cell lines from the pupal tissues of the *L. xylina* and designated as NTU-LY-1, NTU-LY-2, NTU-LY-3, and NTU-LY-4, respectively. From the observation of morphologies, genotype analysis, and isozyme analysis, the four cell lines of NTU-LY-1 to NTU-LY-4 are indeed new cell lines from *L. xyina*. NTU-LY-4 cells showed a faster growth rate than the other three cell lines from the growth curves. All of the newly established cell lines of NTU-LY-1 to NTU-LY-4 were susceptible to the LyxyMNPV from the viral susceptibility test. Furthermore, these cell lines can be infected with LdMNPV-like virus and PenuMNPV virus, and were also susceptible to *Nosema* sp. (isolated from *Eurema blanda*) and *N. bombycis*. The cell lines of the invention can be applied in multiplication of the abovementioned insect-pathogenic microorganisms to produce biopesticides in pest control. In addition, the cell line can also be used as hosts for the expression vectors of said baculovirus to produce recombinant proteins for medical or research purposes. The details of the establishment of cell lines and the corresponding test methods are described in examples as follows:

Example 1

Establishment of Cell Lines from *L. xylina*

The invention isolated 4 cell lines of NTU-LY-1, NTU-LY-2, NTU-LY-3, and NTU-LY-4 from the pupal tissues of *L. xylina*. Among them, the NTU-LY-4 was deposited in Biosource collection and research center (BCRC) of Food Industry Research and Development Institute (FIRDI, 331 Shih-Pin Road, Hsinchu, Taiwan) under an accession number of BCRC 960290 on May 21, 2007.

(1) primary culture

Larvae of *L. xylina* were collected from the low-elevation mountain area located in central Taiwan (Mingjian Township), and reared with leaves of the Formosa sweet gum (*Liquidambar formosana*) at 25° C. The larvae were allowed to go through the pupal stage. The 2-4-day-old pupae were collected and surface-sterilized with a 10% Clorox solution and 70% iodine alcohol. The pupa was cut with an ophthalmic scissors after the pupa was air dried. The internal tissues from each pupa were picked with a fine forceps and a pipet, and placed in a 25 $cm^2$ flask with 2 ml TNM-FH medium containing 100 IU/ml of penicillin (Gibco), 100 mg/ml of streptomycin (Gibco), 1.25 mg/ml of amphotericin B (Sigma), and 16% heat-inactivated fetal bovine serum (FPBS, Hyclone). The primary cultures of pupal tissues were incubated at 28° C. The TNM-FH medium was prepared by adding 228.5 g of Grace's insect cell culture medium (GIBCOTM), 15 g BactoTM TC Yeastolate (Becton, Dicknson and Company), and 15 g Lactalbumin Enzymatic Hydrolysate (Sigma®) into 4740 ml deionized water and then 1.75 g of $NaHCO_3$ was added after the above solution was stirred until a homogeneous suspension is obtained. The pH was adjusted to 6.3 with 10% NaOH. The solution was filtered through a 0.2 μm filter unit (Gelman Laboratory; VacuCap®90Filter unit) at osmolality of 380~400 osm/kg. The medium was incubated at 37° C. for 3 days to confirm no contamination occurred. The sterile medium was stored at 4° C. for future use.

Average cell dimensions were determined from measurements of 30 cells. The results are shown in FIG. 1 and Table 1.

Figure 1:
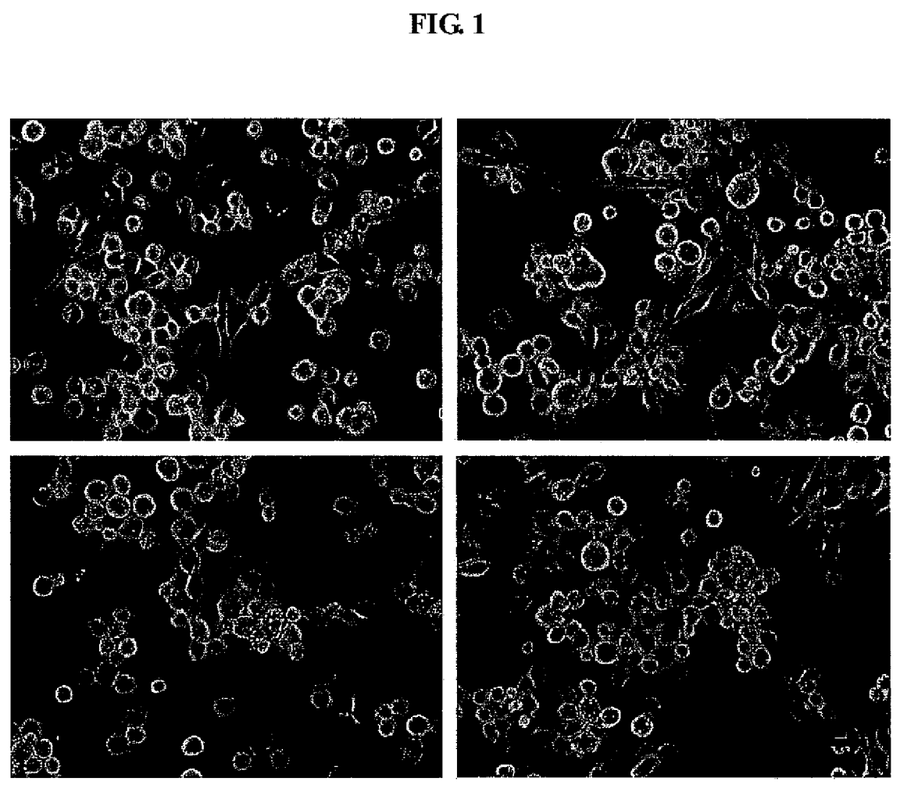
FIG. 1 is cell morphologies of the newly established *L. xylina* cell lines under a phase contrast microscope. (A) NTU-LY-1; (B) NTU-LY-2; (C) NTU-LY-3; and (D) NTU-LY-4. Three major cell types are shown: round cells (R), spindle-shaped cells (Sp), and giant cells (G). All pictures are at the same magnification. Bar, 100 µm.

Referring to FIG. 1, the morphology of these 4 cell lines from *L. xylina* was observed under inverted phase-contrast microscope. Each cell line, NTU-LY-1 to NTU-LY-4, contained 3 cell types: round cells, spindle-shaped cells and giant cells. Slight differences of cell types between these four cell lines were found. Table 1 shows the ratio and the size of each different cell types in the respective cell lines. Among them, NTU-LY-1 contained more giant cells than the other cell lines. NTU-LY-2 and NTU-LY-4 were both typical of spindle-shaped cells, while NTU-LY-3 was characterized by predominantly round cells (92%).

TABLE 1

The ratio of each cell type and the mean size of cells in the four *L. xylina* cell lines

| Cell types | Cell lines | | | |
| --- | --- | --- | --- | --- |
|  | NTU-LY-1 | NTU-LY-2 | NTU-LY-3 | NTU-LY-4 |
| Round cell | 78% (16.9 μm) | 74% (16.5 μm) | 92% (16.8 μm) | 79% (16.4 μm) |
| Spindle-shaped cell | 18% (43.5 μm in length; 13.5 μm in width) | 25% (69.5 μm in length; 12.7 μm in width) | 6% (43.0 μm in length; 13.8 μm in width) | 19% (80.7 μm in length; 12.2 μm in width) |
| Giant cell | 4% (27.3 μm) | 1% (28.1 μm) | 2% (25.0 μm) | 2% (26.3 μm) |

(2) Subculture

The first subculture was performed when the cells reached confluence after 1 month of primary culture. The cells were removed by tapping the bottom of the flask. Two milliliters of suspended cells were transferred to a new 25 $cm^2$ flask containing 4 ml of fresh media (supplemented with antibiotics and FBS). Thereafter, cells were subcultured at 14-day intervals, and the dilution ratio of suspension was gradually increased to 1:4-1:5. The subculture interval then was shortened to 4-7 days. After 25 passages, the cells were adapted to 8% FBS and were routinely subcultured at 5-day intervals.

Finally, four continuous cell lines have been successfully established and are designated NTU-LY-1, NTU-LY-2, NTU-LY-3, and NTU-LY-4, respectively. Among them, the NTU-LY-4 was deposited in Biosource collection and research center (BCRC) of Food Industry Research and Development Institute (FIRDI) under an accession number of BCRC 960290. The approximate passage numbers for the four cell lines during two years were more than 100, indicated good stability for these cell lines. On the other hand, the cell lines according to the invention are not limited to the abovementioned four cell lines. Any other cell lines derived from subcloning or monocloning of the NTU-LY-1 to NTU-LY-4, or other cells lines containing the same or identifiable characteristics are also included in this invention.

Example 2

Cell Morphological Observation

The morphology of cells from individual cell lines of the NTU-LY-1 to NTU-LY-4 were observed under an Olympus IX-71 inverted phase-contrast microscope. Cell sizes were calculated according to a calibrated magnification factor.

Example 3

Growth Curves of the Four Newly Established *L. xylina* Cell Lines

The growth curves of cell lines of NTU-LY-1 to NTU-LY-4 were tested at passage around 80. $1 \times 10^6$ cells from each strain in log phase were seeded into 25 $cm^2$ flasks and cultured in TNM-FH media supplemented with 8% FBS in a 28° C. incubator. Cell numbers were counted under a microscope and the population doubling times were determined (Kuchler, R. J., Development of animal cell populations in vitro. In: Kuchler, R. J. (Ed.), Biochemical Methods in Cell Culture and Virology. Dowden, Hutchingon, and Ross, Inc. Press, Stroudsburg, pp.90-113.1977). The result is shown in FIG. 2.

Figure 2:
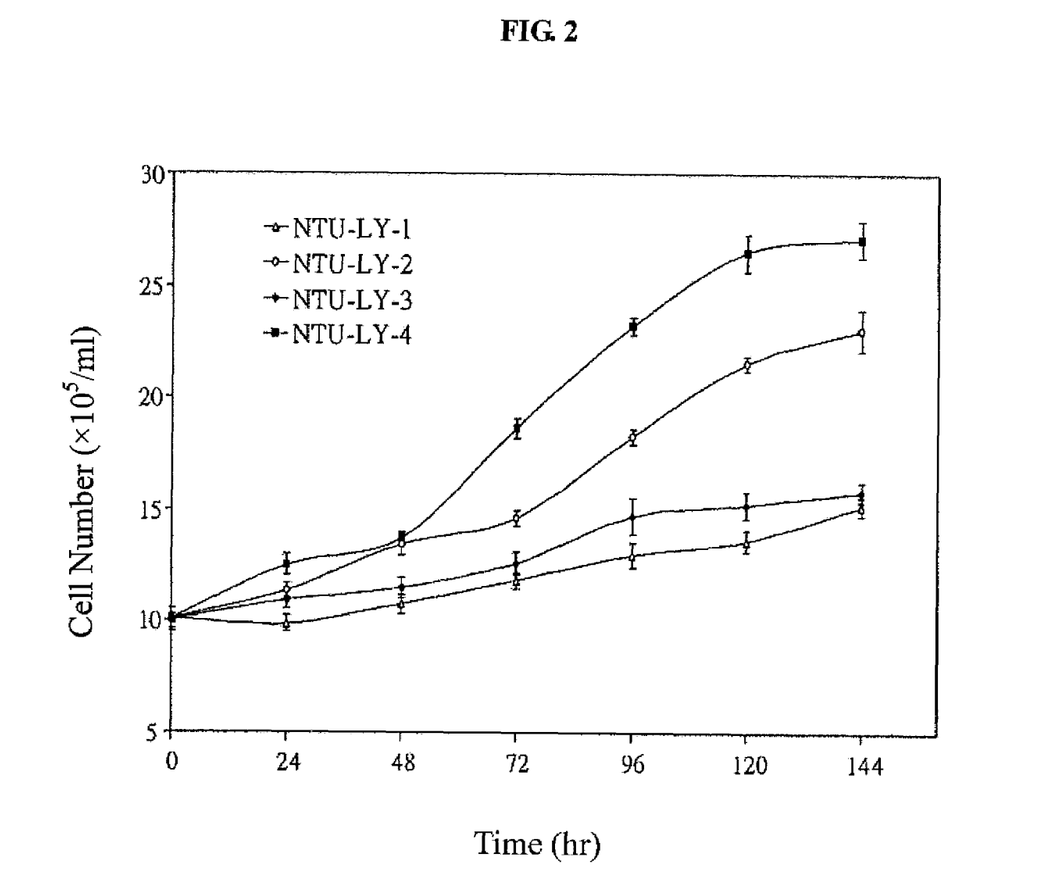
FIG. 2 is Growth curves of the four newly established *L. xylina* cell lines NTU-LY-1 to NTU-LY-4. ∆: NTU-LY-1; ○: NTU-LY-2; ◆: NTU-LY-3; ■: NTU-LY-4. The vertical bars indicate the standard deviation of three independent trials.

Refers to FIG. 2, the growth curves of the 4 cell lines from *L. xylina*. The population doubling times of NTU-LY-1 to NTU-LY-4 were estimated to be 177, 74, 105, and 66 h, respectively. The NTU-LY-4 cells showed the shortest doubling time, which represents a significantly fast growth rate among the 4 cell lines. Cells with a short population doubling time are of more economical value when mass production of the insect cells is needed. The result makes the cell line NTU-LY-4 suitable for the high industrial applications.

Example 4

Genotype Analysis of the *L. xylina* Cell Lines

Random amplified polymorphic DNA-polymerase chain reaction (RAPD-PCR) was performed to identify the origin and genotype of these *L. xylina* cell lines. Random primers are used to anneal with the DNA templates from NTU-LY-1 to NTU-LY-4 randomly to amplify products of polymorphism for the analysis of whole genomes in these cell lines.

Total cell DNA from *L. xylina* larva and the six cell lines, NTU-LY-1 to NTU-LY-4, IPLB-LD-652Y cell line from *L. dispar* (Goodwin, R. H., Tompkins, G. J. and McCawley, P. Gypsy moth cell lines divergent in viral susceptibility. I. Culture and identification. In Vitro.14(6):485-94.1978), and NTU-PN-HH cell line from *Perina nuda* (Wang, C. H., Chou, C. M., Liu, H. C., Kau, S. L., Kou, G. H. and Lo, C. F. Continuous Cell Line from Pupal Ovary of *Perina nuda* (*Lepidoptera: Lymantriidae*) that is permissive to nuclear polyhedrosis virus from *P. nuda*. J. Invertebr. Pathol. 67(3): 199-204.1996) were extracted. Three 10-mer random primers (OPU-09:CCA CAT CGG T (SEQ ID NO: 1), OPU-10:ACC TCG GCA C (SEQ ID NO: 2), and OPO-05:CCC AGT CAC T (SEQ ID NO: 3)) were used for RAPD-PCR. Each PCR consisted of 50 μl mixture, and the mixture contained 50 ng of the abovementioned cellular DNA, 1× reaction buffer (with 2 mM MgSO$_4$), 200 μM dNTP, 2.5 U HiFi DNA polymerase, 1 μM of primer. The PCR was performed under the following conditions: preheating for 2 mm at 94° C.; 40 cycles of 94° C. for 1 mm 40° C. for 1 mm and 72° C. for 2 mm; followed by 72° C. for 15 mm. The PCR products were electrophoresed on 2% agarose gel containing ethidium bromide in TAE buffer. The results are shown in FIG. 3.

Figure 3:
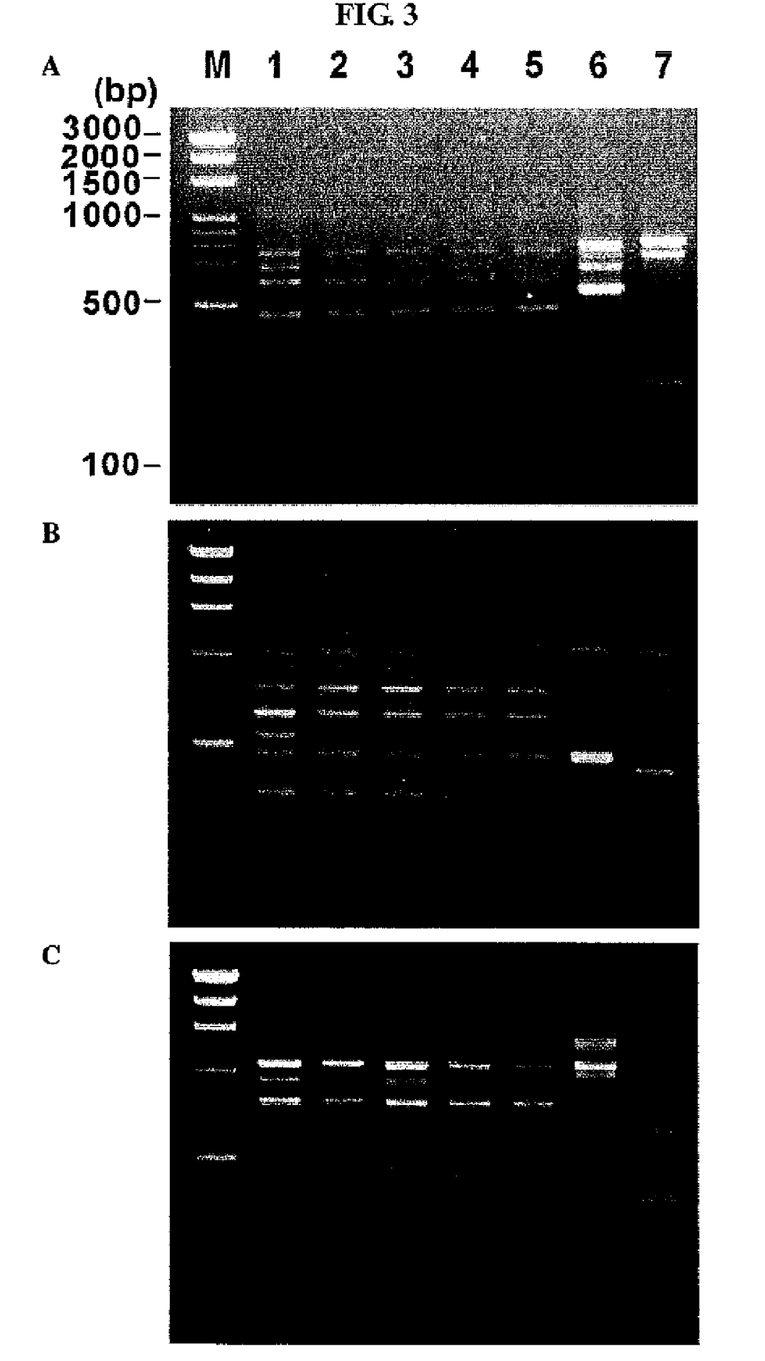
FIG. 3 is RAPD-PCR profile of the four *L. xylina* cell lines, a *L. xylina* larva and other insect cell lines. (A) primer OPU-09 was used for amplification, (B) primer OPU-10 was used for amplification, and (C) primer OPO-05 was used for amplification. Lane M, Gen-100 DNA Ladder (GeneMark), the molecular weight markers (bp) are shown in the left side; Lane 1, *L. xylina* larva; Lane 2, NTU-LY-1; Lane 3, NTU-LY-2; Lane 4, NTU-LY-3; Lane 5, NTU-LY-4; Lane 6, IPLB-LD-652Y; and Lane 7, NTU-PN-HH.

Electrophoresis results from RAPD-PCR profile analysis of *L. xylina* larva, four newly established cell lines from *L. xylina*, IPLB-LD-652Y cell line from *L. dispar* and NTU-PNHH cell line from *Perina nuda* are shown in FIG. 3. Similar DNA profiles were found among the four newly established *L. xylina* cell lines and the *L. xylina* larva, indicated identical genotypes for them. In contrast, the DNA profiles mentioned above were quite distinct from those of the two cell lines, IPLB-LD-652Y and NTU-PN-HH though they belong to the Lymantriidae family. These results indicated that all cells of NTU-LY-1 to NTU-LY-4 are derived from the *L. xylina*.

Example 5

Isozyme Analysis of the *L. xylina* Cell Lines

Isozyme analysis was further employed for determining variation of *L. xylina* cells and cells from other species of the genus *Lymantria*. Enzymes of similar function but different forms (isozymes) can be separated by gel electrophoresis due to differences in structure and physical characteristics. The isozyme variation is used to detect the species difference.

Confluent cells of the cell lines of NTU-LY-1 to NTU-LY-4 from *L. xylina*, and IPLB-LD-652Y cell line from *L. dispar*, were harvested from each culture flask (T25, 25 cm$^2$). The cells were centrifuged at 70×g for 10 min at 4° C., resuspended in 500 μl of grinding buffer (0.125 M Tris—HCl, 46 mM citric acid, 10% sucrose, 1% Triton X-100, and 0.02 mM bromophenol blue), and lysed by 3 freeze/thaw cycles in liquid nitrogen and a 37° C. water bath. The cell lysate was centrifuged at 8500×g for 5 min, and the supernatant was collected as sample solution. For sample separation, 10-20 μl of each sample solution was loaded into a 10% polyacrylamide gel, and electrophoresed at a constant current of 20 mA for 2 h. The gels were tested for the activities of three isozymes: esterase, malate dehydrogenase (MDH), and lactate dehydrogenase (LDH), and the results are shown in FIG. 4.

Figure 4:
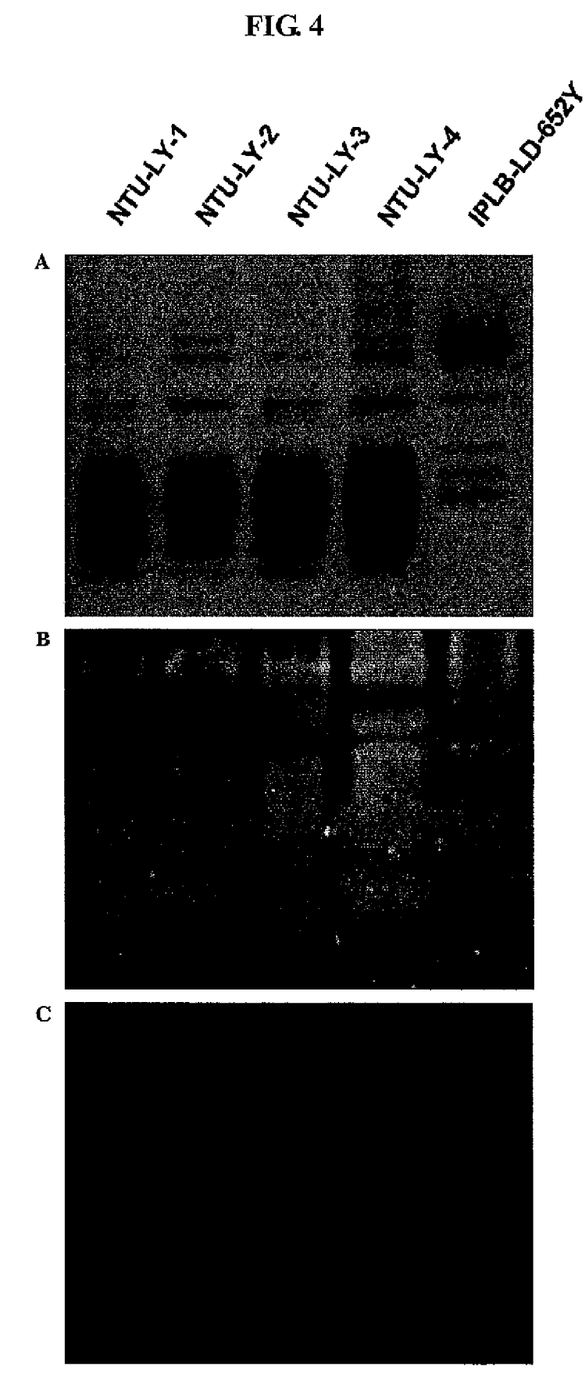
FIG. 4 is the isozyme patterns after electrophoresis analysis of NTU-LY-1 to NTU-LY-4 cell lines from *L. xylina*. (A) Esterase, (B) MDH, and (C) LDH. The cell lines are indicated on top of the pictures correspondingly.

Refers to FIG. 4, the isozyme gel electrophoretic patterns of the 4 cell lines from *L. xylina*, and the cell line from *L. dispar*. The esterase, MDH, and LDH isozyme patterns of NTU-LY-1 to NTU-LY-4 cells from *L. xylina* are similar, but are significantly different from the cell line from *L. dispar*. This indicated that the 4 cell lines from *L. xylina* established in the invention are unique cell lines, which have never been found before, verifying they are new cell lines. On the other hand, the isozyme patterns of NTU-LY-1 to NTU-LY-4 with minor difference can be divided into two groups though they are quite similar in general: NTU-LY-1 and NTU-LY-3 form one group while NTU-LY-2 and NTU-LY-4 form the other group.

Example 6

Viral Susceptibility Analysis of the Newly Established *L. xylina* Cell Lines

The viral susceptibility and cytopathologic changes of the 4 newly established *L. xylina* cell lines to LyxyMNPV and other insect baculovirus were observed under a microscope, and the occlusion body-containing cells were counted to reveal the cell pathological effect and viral pathogenicity. Endpoint dilution assay (Summers, M. D., Smith, G. E. A manual of methods for baculovirus vectors and insect cell culture procedure. Texas Agricultural Experiment Station, No 155.1988) was used to determine 50% tissue culture infective dose (TCID$_{50}$/ml) for qualitative analysis of the budded virus (BV) after viral replication.

(1) Susceptibility Analysis of the *L. xylina* Cell Lines toward Insect Baculovirus The viral susceptibility of NTU-LY-1 to NTU-LY-4 cells were tested against the following virus: AcMNPV (*Autographa californica* NPV), kindly supplied by Dr. M. J. Fraser of Notre Dame University; P MNPV (*P. nuda* NPV), collected from infected NTU-PN-HH cells; LdMNPV-like virus, initially isolated from an infected larva of *L. xylina* and propagated in vitro in IPLB-LD-652Y cells; and LyxyMNPV, collected from an infected larva of *L. xylina*.

Log-phase cells of NTU-LY-1 to NTU-LY-4 were inoculated with culture solutions containing LyxyMNPV, AcMNPV, PenuMNPV, LdMNPV-like virus, respectively. After 1 h of adsorption, the viral solution was discarded and fresh TNM-FH media were added to the cells and cultivated in a 28° C. incubator for 7 days. Occlusion body (OB)-containing cells were observed and counted with an inverted phase-contrast microscope (Olympus IX-71) and the results are shown in FIG. 5 and Table 2.

Figure 5:
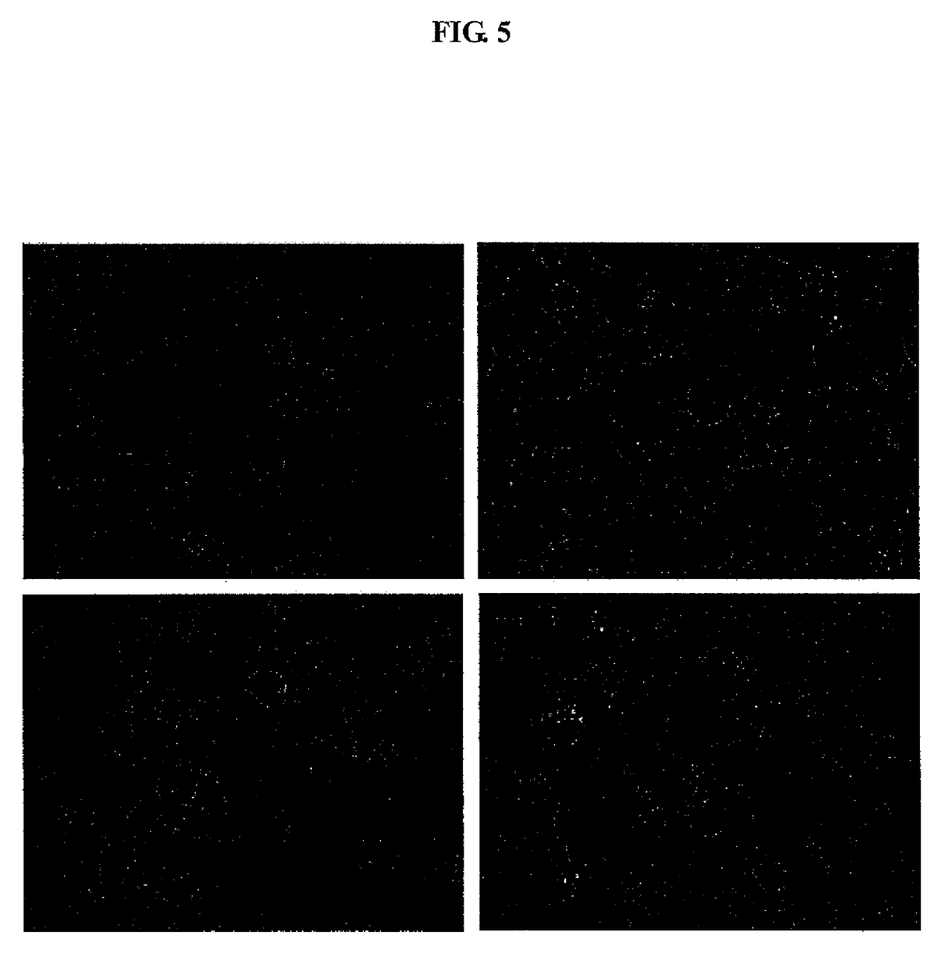
FIG. 5 is cytopathological changes of the four newly established *L. xylina* cell lines NTU-LY-1 to NTU-LY-4 at 7 days post-inoculation with LyxyMNPV. Occlusion bodies(OBs) are indicated by arrows. All pictures are at the same magnification. Bar, 50 µm.

FIG. 5 shows the cytopathologic changes of the four newly established cell lines from *L. xylina*, NTU-LY-1 to NTU-LY-4, after infection with LyxyMNPV. Typical cytopathogenic effects were observed on all the cells after infection, and OBs were seen in the nucleus of some cells. All of the newly established cell lines can be infected by LyxyMNPV, that is, they were susceptible to the LyxyMNPV.

Table 2 shows the viral susceptibility of cell lines from *L. xylina* to various nucleopolyhedroviruses. These cell lines were also susceptible to LdMNPV-like virus and PenuMNPV but not AcMNPV. The table also revealed that NTU-LY-2 and NTU-LY-4 show more severe cytopathologic changes than the other two cell lines, NTU-LY-1 and NTU-LY-3, which refers to a higher susceptibility of NTU-LY-2 and NTU-LY-4.

TABLE 2

The susceptibility of the four newly established *L. xylina* cell lines to various virus

| Viruses | Cell lines | | | |
|---|---|---|---|---|
| | NTU-LY-1 | NTU-LY-2 | NTU-LY-3 | NTU-LY-4 |
| LyxyMNPV | ++ | +++ | ++ | +++ |
| LdMNPV-like virus | ++ | +++ | ++ | +++ |
| PenuMNPV | + | ++ | + | +++ |
| AcMNPV | − | − | − | − |

P.S. +++, over 80% of cells with CPE (OBs);
++, 50-80%;
+, 20-40%;
−, no CPE.

(2) Quantitative Studies of LyxyMNPV

Virus replication was assayed by inoculating $5 \times 10^4$ cells of each cell line (NTU-LY-1 to NTU-LY-4) per well in 0.5 ml of TNM-FH medium supplemented with 8% FBS in 24-well plates (Nunc). Cells from each cell line were inoculated with LyxyMNPV at a multiplicity of infection of 5 as determined by the endpoint dilution assay, and were incubated in a 28° C. incubator for 10 days. Then all cells plus the medium were removed from each well and centrifuged at 1000×g for 10 min. The pellet was resuspended in 950 µl deionized water, and then 50 µl of 10% (w/v) sodium laurel sulfate (Sigma) was added. Cells were disrupted by vortexing, and OBs were counted twice in 100 µl samples using a hemocytometer. The supernatants were used for budded viral titration. Budded virus yields were determined by the endpoint dilution assay and expressed as $TCID_{50}$/ml (50% tissue culture infective dose). The results are shown in Table 3.

The yields of OBs and budded virus produced in the LyxyMNPV production from 4 newly established *L. xylina* cell lines are shown in Table 3. The quantitative results of virus revealed that NTU-LY-2 and NTU-LY-4 were capable of producing more OBs than the other two cell lines, while all the cell lines produced about the similar amounts (around $10^7$ $TCID_{50}$/nl) of budded virus.

TABLE 3

The yields of OBs and budded virus from the LyxyMNPV production in the four newly established *L. xylina* cell lines

| LyxyMNPV | Cell lines | | | |
|---|---|---|---|---|
| | NTU-LY-1 | NTU-LY-2 | NTU-LY-3 | NTU-LY-4 |
| Occlusion bodies (OBs) (mean ± SD) × $10^5$/ml | 7.1 ± 2.2 | 29.5 ± 5.5 | 6.1 ± 3.2 | 21.8 ± 2.6 |
| Budded virus ($TCID_{50}$/ml) | $3.72 \times 10^7$ | $6.31 \times 10^7$ | $2.57 \times 10^7$ | $4.32 \times 10^7$ |

In summary, the susceptibility of the four *L. xylina* cell lines (NTU-LY-1 to NTU-LY-4) to NPV can be applied in the multiplication of the abovementioned virus to produce biopesticides, and in the expression system of said insect baculovirus to produce recombinant proteins for medical or research purposes.

Example 7

Microsporidia Susceptibility Analysis of the *L. xylina* Cell Lines

The susceptibility of the four newly established *L. xylina* cell lines to other insect pathogenic microorganisms was studied. The susceptibility to microsporidia of the cell lines and the pathological morphology in the infected cells were observed under a microscope.

The fat bodies or silk glands from the *N. bombycis* infected silkworms, and the fat bodies from the *Nosema* sp. infected pupal sulfur butterfly (*Eurema blanda*) were removed and inoculated into culture flasks containing cells of NTU-LY-1 to NTU-LY-4 in log phase. The solution was removed after 1 h for absorption and fresh TNM-FH media was added. Cells were cultivated in a 28° C. incubator for 7 to 14 days. Cell morphologies were observed under a Olympus IC-71 microscope and are shown in FIG. 6 and FIG. 7.

Figure 6:
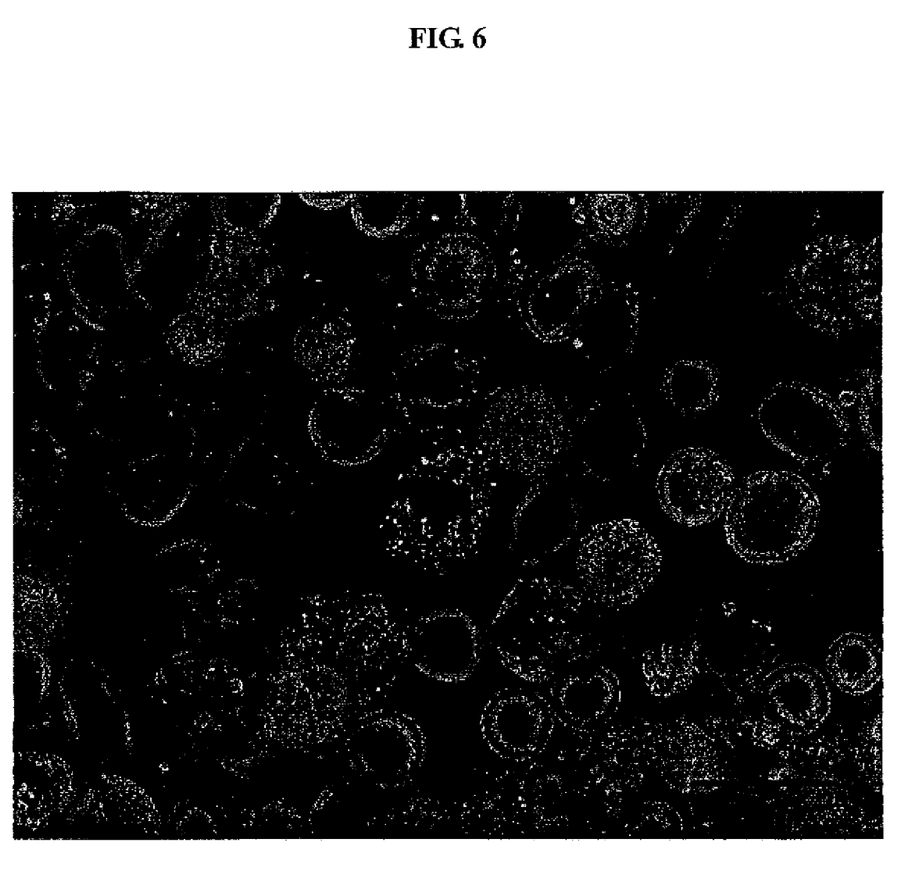
FIG. 6 is cytopathological changes of the newly established *L. xylina* cell lines to NTU-LY-4 at 7 days post-inoculation with *N. bombycis*. Bar, 50 µm.
Figure 7:
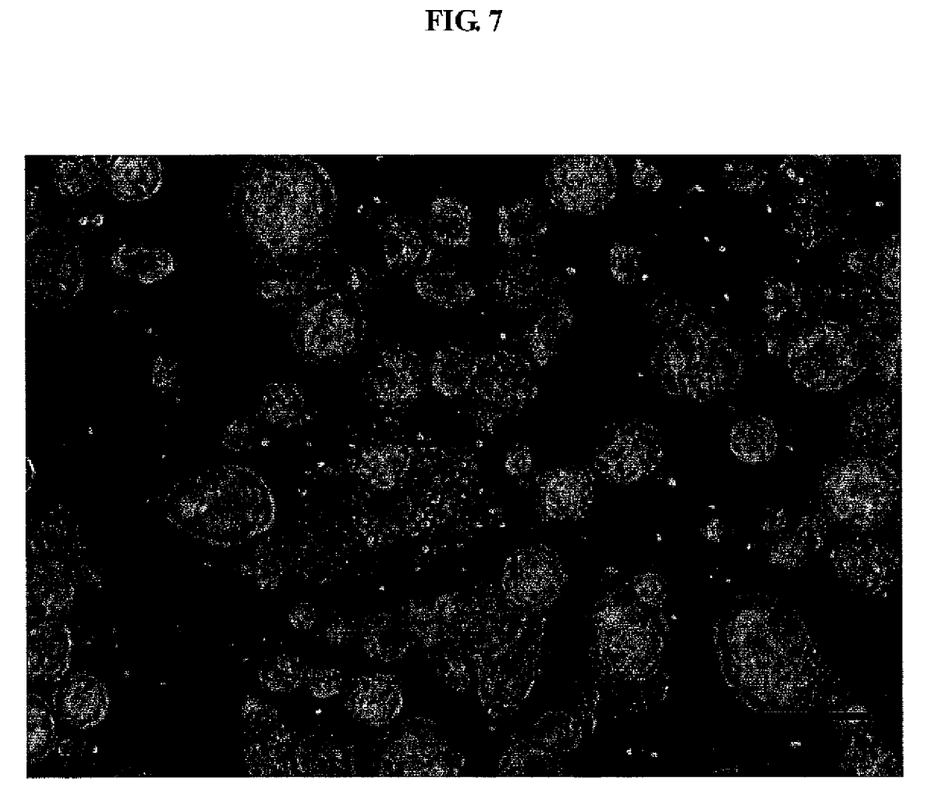
FIG. 7 is cytopathological changes of the newly established *L. xylina* cell lines to NTU-LY-4 at 14 days post-inoculation with Nosema sp. (isolated from *Eurema blanda*). Bar, 50 µm.

The cytopathologic changes to microsporidia of *L. xylina* cells of NTU-LY-1 to NTU-LY-4 were seen in FIG. 6 and FIG. 7 after inoculation of *N. bombycis* and *Nosema* sp. (isolated from *Eurema blanda*). And mature spores were seen in the cytoplasms in some of the infected cells. This shows that the newly established *L. xylina* cell lines can be infected with the abovementioned microsporidia, being susceptible to *N. bombycis* and *Nosema* sp. (isolated from *Eurema blanda*). Therefore *L. xylina* cells of NTU-LY-1 to NTU-LY-4 can be applied in multiplication of at least these two insect microsporidia for biopestides and pest control.

What is claimed is:

1. A *Lymantria xylina* (*L. xylina*) cell line designated NTU-LY-4 deposited in Food Industry Research and Development Institute (FIRDI) under an accession number of BCRC 960290.

2. The *L. xylina* cell line as claimed in claim 1, wherein said NTU-LY-4 cell line is established from the pupal tissues of *Lymantria xylina* Swinhoe.

3. A *Lymantria xylina* (*L. xylina*) cell line, wherein the *L. xylina* cell line is a subclone or monoclonal clone derived from the NTU-LY-4 cell line as claimed in claim 1.

4. The *L. xylina* cell line as claimed in claim 3, wherein said NTU-LY-4 cell line is established from the pupal tissues of *Lymantria xylina* Swinhoe.

5. The *L. xylina* cell line as claimed in claim 1, wherein said NTU-LY-4 cell line has susceptibility to insect-pathogenic microorganisms.

6. The *L. xylina* cell line as claimed in claim 5, wherein said NTU-LY-4 cell line is used for multiplication of insect-pathogenic microorganisms and production of proteins.

7. The *L. xylina* cell line as claimed in claim 6, wherein said insect-pathogenic microorganisms are insect baculovirus comprising LyxyMNPV, LdMNP V-like virus, PenuMNPV and the like.

8. The *L. xylina* cell line as claimed in claim 7, wherein said insect-pathogenic microorganisms further include the baculoviral products from each of the infection stages: budded virus, occlusion bodies, viral DNA and the like.

9. The *L. xylina* cell line as claimed in claim 7, wherein said proteins are the recombinant proteins produced with said insect baculoviral expression vectors in said NTU-LY-4 cell line host cells.

10. The *L. xylina* cell line as claimed in claim 6, wherein said insect-pathogenic microorganisms are microsporidia comprising *Nosema* sp. or *Nosema bombycis*.

11. The *L. xylina* cell line as claimed in claim 10, wherein said *Nosema* sp. is isolated from *Eurema blanda*.

12. The *L. xylina* cell line as claimed in claim 10, wherein said insect-pathogenic microorganisms further include the microsporidia products from each of the infection stages: meronts, spores, DNA and the like.

* * * * *

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Synthetic primer

<400> SEQUENCE: 1
ccacatcggt                                                          10

```
<210> SEQ ID NO 2
<211> LENGTH: 10
<212> TYPE: DNA
<213> ORGANISM: Artificial Sequence
<220> FEATURE:
<223> OTHER INFORMATION: Synthetic primer

<400> SEQUENCE: 2
acctcggcac                                                                  10

<210> SEQ ID NO 3
<211> LENGTH: 10
<212> TYPE: DNA
<213> ORGANISM: Artificial Sequence
<220> FEATURE:
<223> OTHER INFORMATION: Synthetic primer

<400> SEQUENCE: 3
cccagtcact                                                                  10
```